(12) United States Patent
Wang et al.

(10) Patent No.: US 11,938,469 B1
(45) Date of Patent: Mar. 26, 2024

(54) ULTRATHIN LAYER PHOTOCATALYSTS

(71) Applicants: National Technology & Engineering Solutions of Sandia, LLC, Albuquerque, NM (US); Ying-Bing Jiang, Albuquerque, NM (US)

(72) Inventors: Yifeng Wang, Albuquerque, NM (US); Ying-Bing Jiang, Albuquerque, NM (US)

(73) Assignees: National Technology & Engineering Solutions of Sandia, LLC, Albuquerque, NM (US); Ying-Bing Jiang, Albuquerque, NM (US)

( * ) Notice: Subject to any disclaimer, the term of this patent is extended or adjusted under 35 U.S.C. 154(b) by 306 days.

(21) Appl. No.: 16/895,507

(22) Filed: Jun. 8, 2020

(51) Int. Cl.
*B01J 35/00* (2006.01)
*B01J 21/06* (2006.01)
*B01J 35/08* (2006.01)
*B01J 35/10* (2006.01)
*A61L 2/08* (2006.01)
*A61L 2/10* (2006.01)
*A61L 9/20* (2006.01)
*C02F 1/72* (2023.01)

(52) U.S. Cl.
CPC ........... *B01J 35/004* (2013.01); *B01J 21/063* (2013.01); *B01J 35/08* (2013.01); *B01J 35/1009* (2013.01); *A61L 2/084* (2013.01); *A61L 2/088* (2013.01); *A61L 2/10* (2013.01); *A61L 9/205* (2013.01); *C02F 1/725* (2013.01); *C02F 2305/10* (2013.01)

(58) Field of Classification Search
None
See application file for complete search history.

(56) References Cited

U.S. PATENT DOCUMENTS

| 8,758,713 | B2* | 6/2014 | Yoshida | B01J 35/004 |
| | | | | 423/247 |
| 11,179,694 | B2* | 11/2021 | Darji | C01B 13/145 |
| 2004/0065174 | A1* | 4/2004 | Dagenais | E21B 19/164 |
| | | | | 81/57.18 |
| 2008/0118744 | A1* | 5/2008 | Kitamura | B01J 37/0219 |
| | | | | 428/335 |
| 2013/0052117 | A1* | 2/2013 | Imai | C04B 38/0054 |
| | | | | 423/335 |

(Continued)

FOREIGN PATENT DOCUMENTS

JP 2002166176 A * 6/2002
JP 2011005389 A * 1/2011

(Continued)

OTHER PUBLICATIONS

JP-2002166176-A, English translation (Year: 2002).*

(Continued)

*Primary Examiner* — Stefanie J Cohen
(74) *Attorney, Agent, or Firm* — Daniel J. Jenkins

(57) ABSTRACT

A transparent ceramic substrate is covered by a photocatalyst layer, at least partially. The photocatalyst layer includes a semiconductor material that, upon exposure to electromagnetic radiation, forms a plurality of electrons and a plurality of holes that remain confined to the photocatalyst layer. The transparent ceramic substrate has a diameter that is larger than the wavelength of the electromagnetic radiation for light trapping.

6 Claims, 3 Drawing Sheets

(56) References Cited

U.S. PATENT DOCUMENTS

2013/0078458 A1* 3/2013 Biver ............... B05D 3/065
428/336
2020/0139304 A1* 5/2020 Saha ............... B01D 69/105

FOREIGN PATENT DOCUMENTS

WO   WO-2015028818 A1 * 3/2015   ............. A01N 25/08
WO   WO-2017187152 A1 * 11/2017

OTHER PUBLICATIONS

Ida et al, TiO2 coating on silica particles by deposition of sol-gel-derived nanoparticles, advanced powder technol., vol. 18, No. 3, pp. 329-348 (Year: 2007).*

Jung et al, photocatalytic activities and specific surface area of TiO2 films prepared by CVD and sol-gel method, Korean J. Chem, Eng., 25(2), pp. 364-367 (Year: 2008).*

JP-2011005389-A. English translation (Year: 2011).*

Kazuhito Hashimoto et al, TiO2 Photocatalysis: A Historical Overview and Future Prospects, Japanese Journal of Applied Physics, Dec. 8, 2005, 8269-8285, vol. 44, No. 12, The Japan Society of Applied Physics, Japan.

Ramesh Thiruvenkatachari et al, A Review on UV/TiO2 Photocatalytic Oxidation Process, Korean Journal of Chemical Engineering, Jan. 2008, 64-72, vol. 25, Issue 1, Springer, South Korea.

Huifang Xu et al, Photocatalytic Oxidation of a Volatile Organic Component of Acetaldehyde Using Titanium Oxide Nanotubes, Journal of Nanomaterials, Dec. 22, 2006, 1-8, vol. 2006, Hindawi Publishing Corporation, Great Britain.

Liang-Shu Zhong et al, Facile Synthesis of Nanoporous Anatase Spheres and Their Environmental Applications, Chemical Communications, Jan. 11, 2008, 1184-1186, vol. 2008, Issue 10, Royal Society of Chemistry, Great Britain.

* cited by examiner

ULTRATHIN LAYER PHOTOCATALYSTS

STATEMENT REGARDING FEDERALLY SPONSORED RESEARCH OR DEVELOPMENT

This invention was developed under Contract No. DE-NA0003525 awarded by the United States Department of Energy/National Nuclear Security Administration. The Government has certain rights in this invention.

BACKGROUND OF THE INVENTION

The present invention is generally directed to ultrathin layer photocatalysts and more particularly to reusable photocatalyst particles that can be separated from aqueous media with ease for use in sterilization, water treatment, antibacterial, hydrogen production, water purification, air purification, and self-cleaning, such as building exterior self-cleaning, applications.

Photocatalysts are materials and/or material systems that decompose detrimental substances in the presence of electromagnetic radiation, such as ultraviolet light. Titanium oxides, particularly titanium dioxide ($TiO_2$), are semiconductor materials that can function as photocatalysts in various water-related photocatalytic processes.

Pure anatase $TiO_2$ has a band gap of 3.2 eV. When pure anatase $TiO_2$ is irradiated with UV light, an electron is excited from the valence band. In the presence of water, the electron and its corresponding hole in the valence band can split the water into a proton and a hydroxyl radical. The proton and the hydroxyl radical can be used in decomposition of organic contaminants in water through advanced oxidation processes.

Additionally, $TiO_2$ nanoparticles or nanotubes can have high photocatalytic capabilities, partly due to such material systems having high specific surface areas. Such nanoparticles can be used in suspension within a liquid as photocatalysts. Unfortunately, the suspended nanoparticles are difficult to remove from the liquid after use because the particles are so small.

In some applications, $TiO_2$ nanoparticles or nanotubes can be immobilized on a support and/or substrate. However, the immobilization of the nanoparticles or the nanotubes reduces the effective surface area of the photocatalytic material, which reduces the overall reactivity of the material.

What is needed is a high-performance photocatalyst material that has a higher reactivity per surface area. The teachings disclosed extend to those embodiments that fall within the scope of the claims, regardless of whether they accomplish one or more of the aforementioned needs.

SUMMARY OF THE INVENTION

One embodiment relates to an apparatus that includes a transparent ceramic substrate and a photocatalyst layer covering the transparent ceramic substrate, at least partially. The photocatalyst layer includes a semiconductor material that, upon exposure to electromagnetic radiation, forms a plurality of electrons and a plurality of holes that remain confined to the photocatalyst layer. The transparent ceramic substrate has a diameter that is larger than the wavelength of the electromagnetic radiation.

Another embodiment relates to a method for forming a catalyst activated by electromagnetic radiation. A semiconductor material is deposited on a transparent ceramic substrate that has a diameter that is larger than the wavelength of the electromagnetic radiation to cover the ceramic substrate, at least partially, with a photocatalyst layer. The semiconductor material is exposed to the electromagnetic radiation to produce a plurality of electrons and a plurality of holes that remain confined to the photocatalyst layer.

Yet another embodiment relates to a method for treating an aqueous medium with photocatalytic particles and electromagnetic radiation. A plurality of photocatalytic particles is immersed into the aqueous medium with each of the photocatalytic particles having an outer layer of semiconductor material covering, at least partially, an inner layer of transparent ceramic material and having a diameter that is larger than the wavelength of the electromagnetic radiation. The semiconductor material is exposed to the electromagnetic radiation to produce a plurality of electrons and a plurality of holes that remain confined to the photocatalyst layer. A plurality of hydroxyl radicals is formed with the plurality of electrons within the aqueous medium to initiate a plurality of treatment reactions within the aqueous medium.

Alternative exemplary embodiments relate to other features and combinations of features as can be generally recited in the claims.

BRIEF DESCRIPTION OF THE DRAWINGS

The application will become more fully understood from the following detailed description, taken in conjunction with the accompanying figures, wherein like reference numerals refer to like elements, in which.

DETAILED DESCRIPTION OF THE INVENTION

Before turning to the figures which illustrate the exemplary embodiments in detail, it should be understood that the application is not limited to the details or methodology set forth in the following description or illustrated in the figures. It should also be understood that the phraseology and terminology employed herein is for the purpose of description only and should not be regarded as limiting. Unless otherwise indicated percentages are expressed by weight.

Exemplary embodiments of the invention relate to photocatalyst particles that can be formed by depositing ultrathin layers of semiconductor materials on transparent ceramic substrates. The resulting particles can exhibit an extremely high photocatalytic capability (i.e., greater than 1000 times higher than commercial semiconductor nanoparticles) for oxidizing organic compounds in water under the irradiation of ultraviolet light. In some embodiments, the particles can range in size from about 1 millimeter to about 0.1 millimeter.

Figure 1:
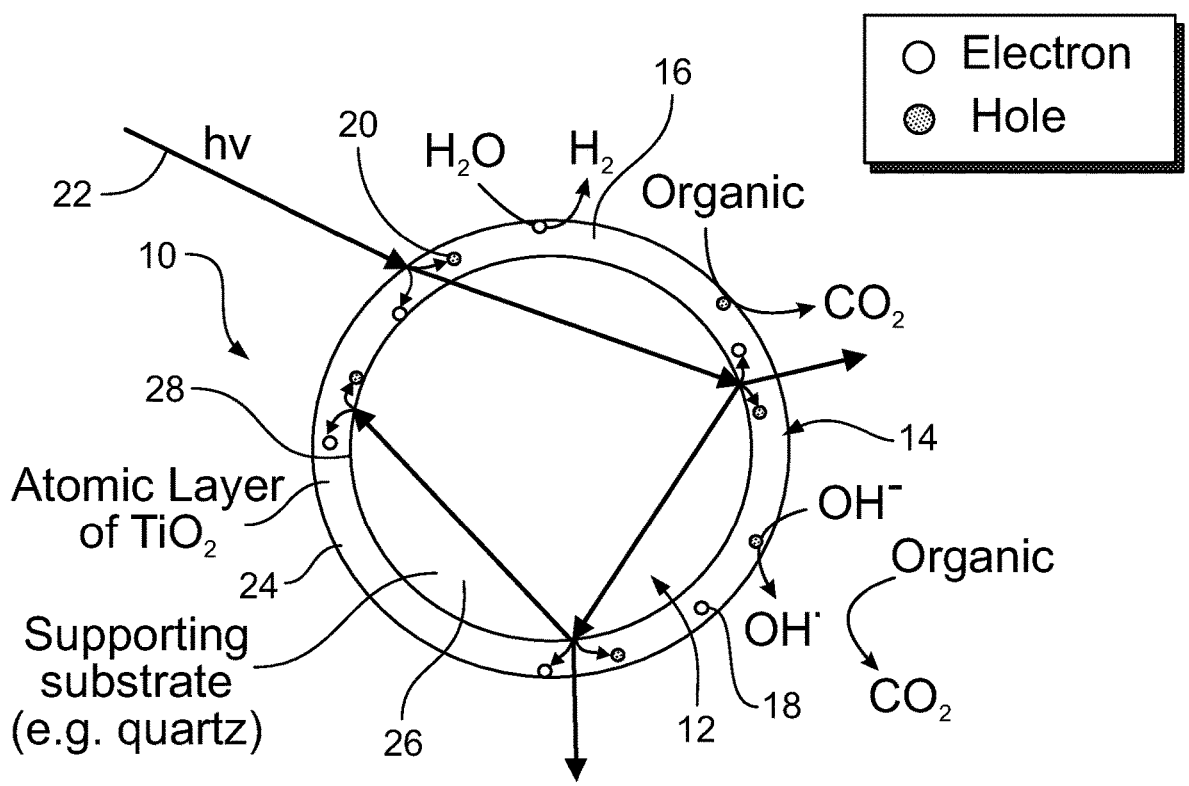
FIG. 1 schematically depicts a photocatalyst apparatus in accordance with the subject matter of the disclosure.

Turning to FIG. 1, a photocatalyst particle, generally designated by the numeral 10, is shown. The photocatalyst particle 10 is relatively large, which provides for easy after-use separation, as compared to conventional nanoparticles. The photocatalyst particle 10 can be used with other similar particles (not shown) in sterilization, water treatment, antibacterial, hydrogen production, water purification, air purification, and self-cleaning, such as building exterior self-cleaning, applications. In one embodiment, application of the photocatalyst may be used for hydrogen production, by splitting water molecules using UV light and solar radiation as shown in FIG. 1, in addition to water treatment.

The particle 10 can have a layered structure having a substrate or a support 12 that is covered by an ultrathin photocatalyst layer 14, at least partially. The ultrathin photocatalyst layer 14 can be formed from a monolayer or from multiple atomic layers, so that the ultrathin photocatalyst layer 14 will typically have a thickness that is less than five nanometers.

The ultrathin photocatalyst layer 14 can include a semiconductor material 16 that forms a plurality of electrons 18 and a plurality of holes 20 upon exposure to electromagnetic radiation 22. The plurality of electrons 18 and the plurality of holes 20 remain confined to the ultrathin photocatalyst layer 14 upon creation. The electrons and the holes are accessible for catalytic reactions at outer surface 24 of the ultrathin photocatalyst layer 14.

The ultrathin photocatalyst layer 14 can be deposited on the substrate 12 through vapor deposition or other methods. After the ultrathin photocatalyst layer 14 is deposited on the substrate 12, the plurality of electrons 18 and the plurality of holes 20 can migrate within the photocatalyst layer 14. Then, the electrons and the holes can migrate through the photocatalyst layer 14 to an outer surface 24 for use in treatment reactions when the photocatalyst particle 10 is immersed in an aqueous medium.

The confinement of the electrons and the holes to the photocatalyst layer 14 differentiates the photocatalytic particle 10 from conventional atomic layer catalysts. In such materials, such as $TiO_2$ nanoparticles, the electrons and the holes that are generated on a nanoparticle surface will migrate towards the inside of the nanoparticle and eventually recombine with one another. The inability to confine electrons and holes to an outer layer can result in a significant loss of material reactivity.

The treatment reactions, generally, are oxidation reactions that oxidize organic compounds within the aqueous medium. A typical reaction sequence involves forming electrons and holes within the ultrathin catalyst layer 14. The electrons react with oxygen molecules to form oxygen radicals. The holes react with organic compounds within the aqueous medium to form carbon dioxide. The holes separate water molecules into protons and hydroxyl radicals. The hydroxyl radicals react with the organic compounds to form carbon dioxide. Then, the photocatalyst particle 10 can be removed from the aqueous medium, dried, filtered, and re-used with the ultrathin photocatalyst layer 14 being reactivated, as needed.

The substrate 12 includes a supporting ceramic material 26 that has a compatible structure and/or a similar structure as the semiconductor material 16, so that monolayers or atomic layers can be formed on an outer surface 28 of the supporting ceramic material 26. The compatibility and/or similarity of the structure of the semiconductor material 16 to the structure of the supporting ceramic material 26 provides stability in a catalytic process. It should be understood that types of structures for the semiconductor material 16 and/or the supporting ceramic material 26 can include "amorphous" structures and/or structures that have short-range order.

The supporting ceramic material 26 can include any suitable ceramic material. The supporting ceramic material 26 must be transparent to the electromagnetic radiation 22 to activate a target photocatalytic reaction, such as oxidizing organic compounds in water.

The crystallinity of the ceramic material can range from highly oriented to semi-crystalline, vitrified, and amorphous. Suitable materials include transparent ceramic materials, such as transparent glasses, silicon, quartz, silica oxide, and aluminum oxide. The ceramic material can include magnetite to impart magnetic properties to the photocatalyst particle 10 to enhance the ability to separate the photocatalyst particle 10 from an aqueous media.

The photocatalyst layer 14 can be made from a nanostructured photocatalytic material with a structure that is compatible with the structure of the ceramic material contained within the substrate 12, at least at an interface 28 between the substrate 12 and the photocatalyst layer 14. The photocatalyst layer 14 can include a semiconductor, such as titanium dioxide ($TiO_2$), cerium dioxide ($CeO_2$) and their solid solutions ($CeO_2$—$TiO_2$). The substrate 12 can include coarse grained quartz, which has a compatible structure with titanium dioxide. The combination of titanium dioxide and quartz can produce a particle that has a specific surface area of less than 0.02 square meters per gram.

The supporting ceramic material 26 can have particle size or diameter that must be larger than the wavelength of the electromagnetic radiation 22. In some embodiments, the wavelength of electromagnetic radiation 22 can be between about 10 nanometers to about 700 nanometers. In other embodiments, the particle 10 has diameter that is between about 1 millimeter to about 0.1 millimeter.

The transparency of the supporting ceramic material 26 coupled with the size of the particle 10 induces multiple reflections and refractions within the particle 10 (or between the particle 10 and a neighboring particle (not shown)). These reflections and refractions help trap the light and therefore increase the efficiency of photocatalytic reactions. For conventional $TiO_2$ nanoparticles, the multiple reflections and refractions may not be possible due to their sizes being much smaller than the wavelength of the radiation.

Figure 2:
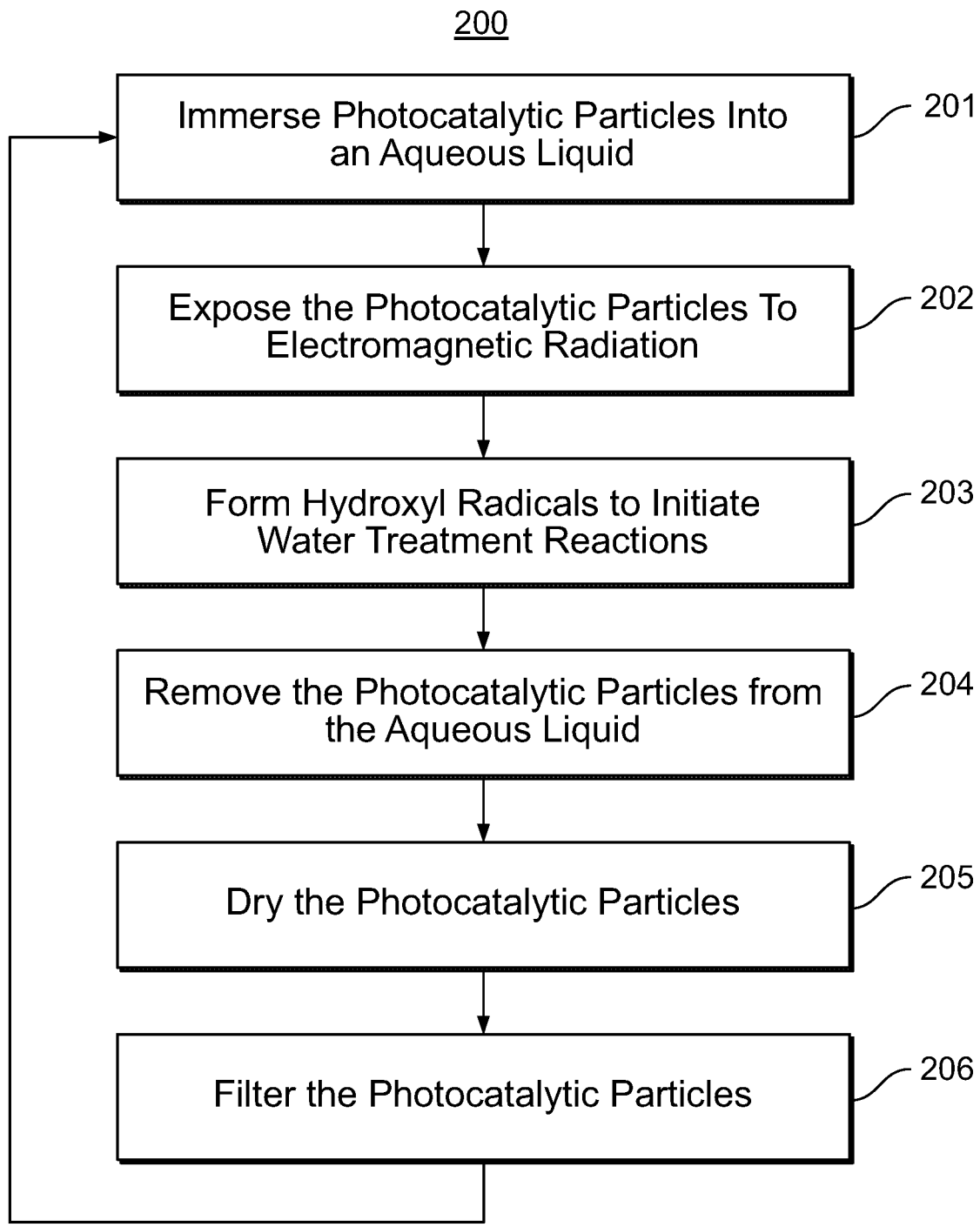
FIG. 2 is a schematic diagram of an exemplary process in accordance with the subject matter of the disclosure.

Referring to FIG. 2 with continuing reference to the foregoing figure, a method 200 is illustrated as an embodiment of an exemplary process for treating an aqueous medium in accordance with features of the described subject matter. The aqueous medium is treated with photocatalytic particles, such as the particle 10 shown in FIG. 1, and electromagnetic radiation, such as the electromagnetic radiation 22 shown in FIG. 1.

At 201, photocatalytic particles are immersed in an aqueous medium. In this exemplary embodiment, the photocatalytic particles have an outer layer of semiconductor material covering, at least partially, the surface of transparent ceramic material. Additionally, the particles have a diameter that is larger than the wavelength of the electromagnetic radiation. The semiconductor material can be the semiconductor material 16 shown in FIG. 1. The ceramic material can be the ceramic material 26 shown in FIG. 1.

At 202, the particles are exposed to electromagnetic radiation. In this exemplary embodiment, the semiconductor material is exposed to the electromagnetic radiation to produce a plurality of electrons and a plurality of holes. The electrons and the holes remain confined to the photocatalyst layer. The plurality of electrons can be the plurality of electrons 18 shown in FIG. 1. The plurality of holes can be the plurality of holes 20 shown in FIG. 1.

At 203, hydroxyl radicals are formed to initiate treatment reactions. In this exemplary embodiment, a plurality of hydroxyl radicals is formed with the plurality of electrons within the aqueous medium to initiate a plurality of treatment reactions within the aqueous medium. The treatment reactions can be reactions in which organic compounds are oxidized within the aqueous medium.

At 204, the particles are removed from the aqueous medium. Then, at 205, the particles can be dried. Then, at 206, the particles can be filtered for reuse, at 201.

Example 1

In example 1, photocatalytic particles were prepared though the vapor deposition of atomic layers of $TiO_2$ on quartz sand using a vapor deposition instrument developed by Angstrom Thin Films Technologies, LLC of Albuquerque, New Mexico. The photocatalytic particles were made using quartz having a grain size of about 300 microns. Precursor (precursor anatase) and nanoporous titanium oxide materials (nonporous anatase) were also prepared for use as control samples.

The precursor anatase samples were prepared by mixing 2 mL of tetrabutoxytitanium and 50 mL of ethylene glycol with a stir plate for 8 hours at room temperature to form an ethylene glycol mixture. An acetone mixture was formed with 2.7 mL of deionized water and 170 mL of acetone. The ethylene glycol mixture and the acetone mixture were combined and stirred at a high speed for an hour to form a tetrabutoxytitanium solution. The tetrabutoxytitanium solution was centrifuged in order to obtain the precipitate, which was then washed with ethanol five times. The precipitate was dried in an oven at 50° C.

The nanoporous anatase samples were prepared from a mixture of 0.1 g of the precursor anatase and 20 mL of deionized water to form a solution. The solution was heated and stirred to reflux for an hour. The solution was centrifuged from reflux. The precipitate was washed with water five times. The precipitate was dried in an oven at 50° C.

All of the samples were tested by subjecting the samples to ultraviolet light. In order to ensure that the ultraviolet light was concentrated directly onto the samples, the beaker and the stir plate were placed within an enclosed metal cabinet. A hole on the side of the metal cabinet allowed a lens for an ultraviolet lamp to be directed into the samples.

An Oriel light source (Hg—Xe 1000 Watts) was used in an Oriel arc lamp (Model #66073) with an Oriel Light Intensity Controller (Model #68850) at 900 watts, which were obtained from Oriel Lighting Pty Ltd of Brisbane, Australia. A water infrared filter was used to minimize heat gain during the experiment. The samples were located in the light path at a distance of 33 cm on a stir plate.

Methyl Orange dye ($8.55 \times 10^{-6}$ M in DI $H_2O$) was used as an indicator. The dye has an absorbance peak at 470 nanometers. A small amount of sample was added to a clean dry Erlenmeyer flask. 150 mL of $8.55 \times 10^{-6}$ M Methyl Orange was added to the flask with a stir bar. The solution was capped and stirred for a minimum of 1 hour in ambient conditions.

Once the lamp was turned on, the lamp intensity and the temperatures of the samples were monitored. Measurements were taken every ten minutes for ninety minutes. The samples were then centrifuged and an ultraviolet spectrum of the solution was taken, noting the absorbance of the solution at 470 nm. Beer's Law was applied to extract the percentage of dye remaining in each sample.

The test results indicated that the photocatalytic particles have extremely high surface-normalized reactivity for photocatalytic reactions (>1000 times higher than commercial $TiO_2$ nanoparticles) and a specific surface area of less than 0.02 square meters per gram. The photocatalytic particles were shown to be recoverable from solution and to be able to provide this same photocatalytic efficiency upon reuse.

Example 2

Figure 3:
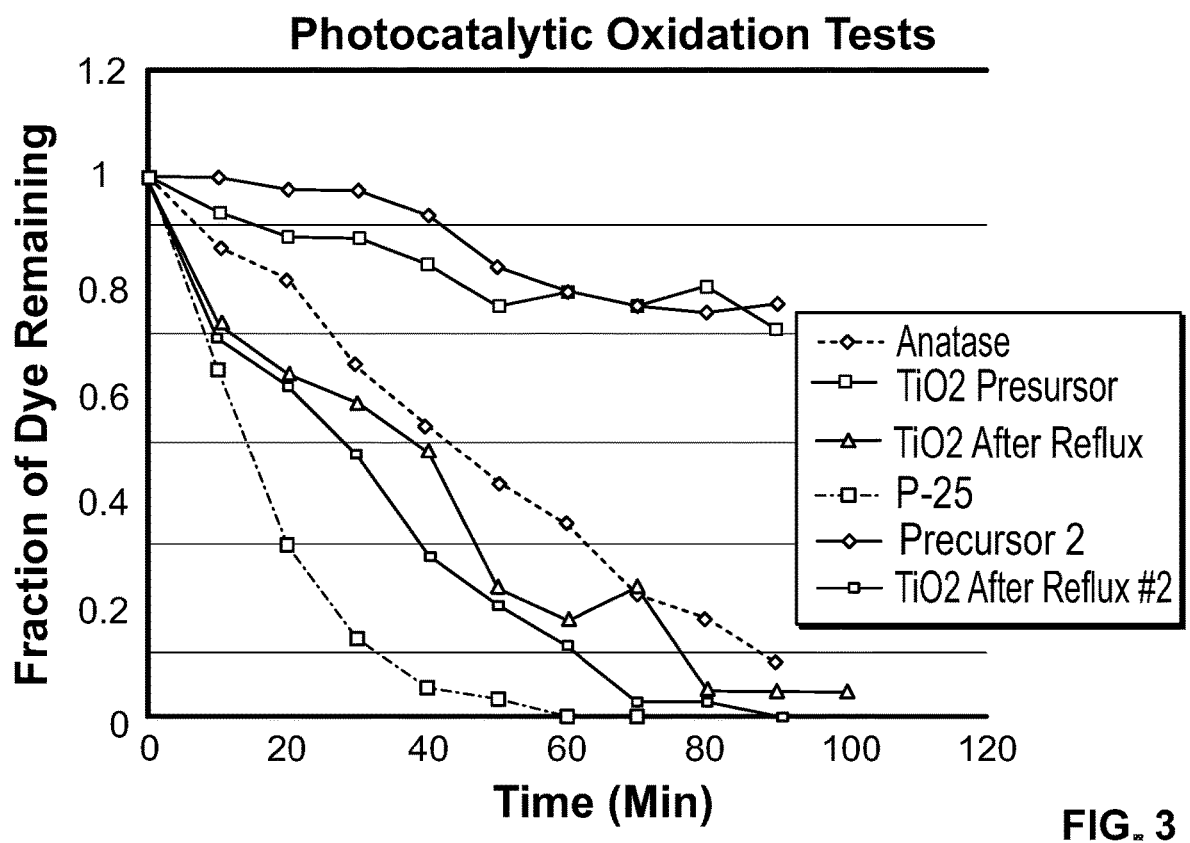
FIG. 3 is a graph illustrating photocatalytic oxidation tests for certain photocatalyst samples prepared in accordance with the subject matter of the disclosure.
Figure 4:
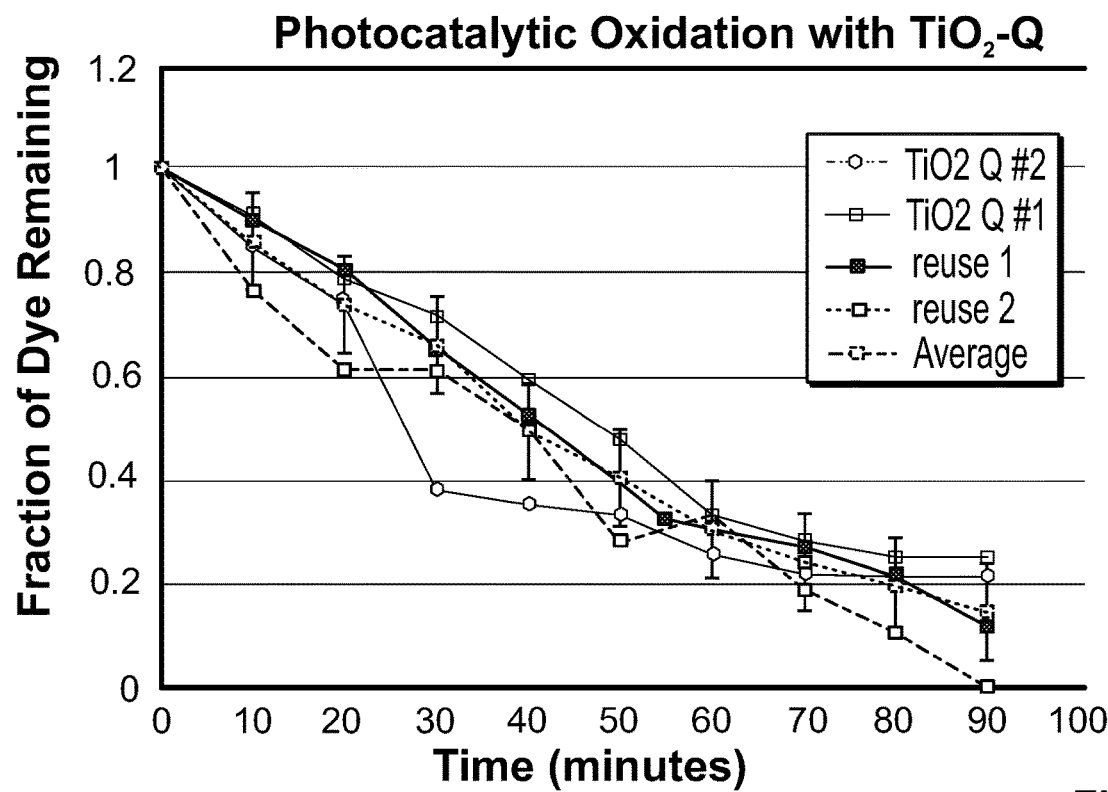
FIG. 4 is a graph illustrating photocatalytic oxidation tests showing the performance of samples that have been reactivated.

In Example 2, the samples from Example 1 were characterized with additional control materials though oxidation tests with the results being shown in FIGS. 3-4. FIG. 3 shows that precursor titania samples display poor photocatalytic behavior by degrading 20% of the dye in 90 minutes. The titania samples were exposed to a reflux environment ($TiO_2$ After Reflux) and degraded between about 90% and about 100% of the dye in 90 minutes, which is better than anatase $TiO_2$. The anatase $TiO_2$ control materials were obtained from Sigma-Aldrich Corporation of St. Louis, Missouri.

Another set of control material were P25 materials. P25 materials are a Degussa product that were obtained from Evonik Industries AG of Essen, Germany. The P25 materials contain a proprietary mix of anatase and rutile $TiO_2$ and is considered the industry standard. The P25 control material was observed to be most effective by degrading the methyl orange dye in less than 60 minutes of lamp exposure.

FIG. 4 shows that the photocatalytic particles provided photocatalytic behavior that was comparable to the anatase and the $TiO_2$ After Reflux control samples. The photocatalytic particles were filtered and washed before reuse to ensure that the particles were durable. The photocatalytic particle-reuse samples showed comparable photocatalytic behavior to that of the original samples.

The surface area of the photocatalytic particles and the photocatalytic particle reuse samples was $\frac{1}{1000}$th of the surface area of one of the control materials. More surface area correlates with more contact between the particle and the dye molecules. A low surface area sample should not be as effective in photocatalytic oxidation. Normalized the surface area, the reactivity of an atomic layer catalyst in the photocatalytic particles is roughly three orders of magnitude higher than other materials including nanoparticles. The comparable performance of the photocatalytic particles was unexpected.

While the exemplary embodiments illustrated in the figures and described herein are presently preferred, it should be understood that these embodiments are offered by way of example only. Accordingly, the present application is not limited to a particular embodiment but extends to various modifications that nevertheless fall within the scope of the appended claims. The order or sequence of any processes or method steps can be varied or re-sequenced according to alternative embodiments.

It is important to note that the construction and arrangement of the desalinization membranes as shown in the various exemplary embodiments is illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited in the claims. For example, elements shown as integrally formed can be constructed of multiple parts or elements, the position of elements can be reversed or otherwise varied, and the nature or number of discrete elements or positions can be altered or varied. Accordingly, all such modifications are intended to be included within the scope of the present application. The order or sequence of any process or method steps can be varied or re-sequenced according to alternative embodiments. In the claims, any means-plus-function clause is intended to cover the structures described herein as performing the recited function and not only structural equivalents but also equivalent structures. Other substitutions, modifications, changes and omissions can be made in the design, operating conditions and arrangement of the exemplary embodiments without departing from the scope of the present application.

The invention claimed is:

1. A apparatus comprising:
   a transparent ceramic substrate; and
   a photocatalyst layer covering the transparent ceramic substrate, at least partially;
   wherein the photocatalyst layer includes a semiconductor material that, upon exposure to electromagnetic radiation, forms a plurality of electrons and a plurality of holes that remain confined to the photocatalyst layer;
   wherein the transparent ceramic substrate is spherical and has a diameter that is larger than the wavelength of the electromagnetic radiation;
   wherein the transparent ceramic substrate is a selected from materials that have structures selected from the group consisting essentially of highly oriented crystalline, semi-crystalline, vitrified and amorphous materials;
   wherein the photocatalyst layer comprises a mono or multiple atomic layer and has a thickness of less than 5 nanometers;
   wherein the semiconductor material consists essentially of titanium dioxide, cerium dioxide or a solid solution of titanium dioxide and cerium dioxide;
   wherein the transparent ceramic substrate has a diameter that is between 0.01 millimeter and 1 millimeter; and
   wherein the photocatalyst layer and the transparent ceramic substrate form a particle having a specific surface area of less than 0.02 square meters per gram.

2. The apparatus of claim 1, wherein the wavelength of electromagnetic radiation is between 10 nanometers to 700 nanometers.

3. The apparatus of claim 1, wherein the semiconductor material includes a nanostructured photocatalytic material.

4. The apparatus of claim 1, wherein the transparent ceramic substrate includes a material selected from the group consisting of transparent glass, silicon, quartz, silica oxide, and aluminum oxide.

5. The apparatus of claim 4, wherein the transparent ceramic material includes magnetite.

6. The apparatus of claim 1, wherein the transparent ceramic material has a diameter to induce multiple reflections and refractions of the electromagnetic radiation to increase the efficiency of the semiconductor material.

* * * * *